(12) United States Patent
Payton et al.

(10) Patent No.: US 10,285,987 B2
(45) Date of Patent: May 14, 2019

(54) DEVICE AND KIT FOR DOSING AND DISPENSING NON-LIQUID MEDICINE

(71) Applicant: AmpliPharm Pharmaceuticals, LLC, Johns Creek, GA (US)

(72) Inventors: Gary Payton, Suwanee, GA (US); Frank Francavilla, Wantage, NJ (US)

(73) Assignee: AmpliPharm Pharmaceuticals, LLC, Johns Creek, GA (US)

( * ) Notice: Subject to any disclaimer, the term of this patent is extended or adjusted under 35 U.S.C. 154(b) by 0 days.

(21) Appl. No.: 15/843,205

(22) Filed: Dec. 15, 2017

(65) Prior Publication Data

US 2018/0311234 A1  Nov. 1, 2018

Related U.S. Application Data

(63) Continuation-in-part of application No. 15/581,677, filed on Apr. 28, 2017, now Pat. No. 10,098,874.

(51) Int. Cl.
*B65D 83/06* (2006.01)
*A61K 31/495* (2006.01)
(Continued)

(52) U.S. Cl.
CPC .......... *A61K 31/495* (2013.01); *A61K 9/0053* (2013.01); *A61K 9/1611* (2013.01);
(Continued)

(58) Field of Classification Search
CPC ...................................................... B65D 83/06
See application file for complete search history.

(56) References Cited

U.S. PATENT DOCUMENTS 4,587,846 A   5/1986 Coma Julia
4,609,371 A   9/1986 Pizzino
(Continued)

FOREIGN PATENT DOCUMENTS

EP   2939662      11/2015
EP   2939662 A1   11/2015
(Continued)

OTHER PUBLICATIONS

International Search Report and Written Opinion for PCT Application No. PCT/US2017/066824.
(Continued)

*Primary Examiner* — Carlos A Azpuru
(74) *Attorney, Agent, or Firm* — Fortunato IP Law, LLC; David M. Fortunato

(57) ABSTRACT

A device for dosing and dispensing a dose of a non-liquid medicine that comprises a body connectable to a container containing an amount of a non-liquid medicine. When the body is connected with the container, an amount of the non-liquid medicine may be transferred from the container to at least one chamber defined within the body. In a preferred embodiment, two chambers are defined within the body, each having a different predetermined size (i.e., volume). A user may set the amount of the non-liquid medicine to be transferred using a plunger rod slideably located within the at least one chamber, or with each of the two chambers. A kit comprises the device and a non-liquid medicine that is readily dispersible in an aqueous solution suitable for oral administration, preferably a temozolomide formulation that can be titrated readily and accurately.

13 Claims, 8 Drawing Sheets

(51) Int. Cl.
  *A61K 9/00* (2006.01)
  *A61K 9/51* (2006.01)
  *A61K 9/50* (2006.01)
  *A61K 9/16* (2006.01)

(52) U.S. Cl.
  CPC .......... *A61K 9/1641* (2013.01); *A61K 9/5026* (2013.01); *A61K 9/5115* (2013.01); *A61K 9/5123* (2013.01); *B65D 83/06* (2013.01)

(56) References Cited

U.S. PATENT DOCUMENTS

| | | |
|---|---|---|
| 4,610,666 A | 9/1986 | Pizzino |
| 4,779,770 A | 10/1988 | Herold |
| 5,143,261 A | 9/1992 | Drobish |
| 5,253,785 A | 10/1993 | Haber et al. |
| 5,351,683 A | 10/1994 | Chiesi et al. |
| 5,441,175 A | 8/1995 | Jacobsen et al. |
| 5,460,617 A | 10/1995 | Minkus et al. |
| 5,496,284 A | 3/1996 | Waldenburg |
| 5,520,658 A | 5/1996 | Holm |
| 5,622,721 A | 4/1997 | Dansereau et al. |
| 6,250,504 B1 | 6/2001 | Maffei |
| 8,074,843 B2 | 12/2011 | Keller |
| 8,353,866 B2 | 1/2013 | Evans, Jr. |
| 8,834,848 B2 | 9/2014 | Muellinger et al. |
| 8,888,751 B2 | 11/2014 | Mudd |
| 9,119,919 B2 | 9/2015 | Manke et al. |
| 9,452,263 B2 | 9/2016 | Grunhut |
| 9,498,577 B2 | 11/2016 | Skaper et al. |
| 2001/0006650 A1 | 7/2001 | Burnside et al. |
| 2005/0096365 A1 | 5/2005 | Fikstad et al. |
| 2008/0142554 A1* | 6/2008 | Lafferty ................ A61M 5/001 222/566 |
| 2008/0171084 A1 | 7/2008 | Vanderbist et al. |
| 2009/0012184 A1 | 1/2009 | Rosenberg et al. |
| 2010/0297194 A1 | 11/2010 | Catron et al. |
| 2017/0028135 A1 | 2/2017 | Fransson et al. |
| 2017/0209680 A1 | 7/2017 | Lin et al. |

FOREIGN PATENT DOCUMENTS

| | | | |
|---|---|---|---|
| KR | 16-206-0060462 | * | 6/2010 |
| KR | 1020100060462 A | | 6/2010 |

OTHER PUBLICATIONS

International Search Report Issued in PCT/US2017/030112 dated Aug. 4, 2017.

* cited by examiner

DEVICE AND KIT FOR DOSING AND DISPENSING NON-LIQUID MEDICINE

CROSS-REFERENCE TO RELATED APPLICATIONS

This application is a Continuation-In-Part of U.S. patent application Ser. No. 15/581,677, filed on Apr. 28, 2017, which claims the benefit of U.S. Provisional Patent Application No. 62/328,929, filed on Apr. 28, 2016, each of which are hereby incorporated herein by reference.

FIELD OF THE INVENTION

The present invention relates to a device for dosing and dispensing a dose of a non-liquid medicine, and a kit comprised of the device and the non-liquid medicine.

BACKGROUND OF THE INVENTION

Temozolomide, an alkylating drug, is marketed in the U.S. as TEMODAR® for the treatment of adult patients with newly diagnosed glioblastoma multiforme (GBM) concomitantly with radiotherapy and then as maintenance treatment. Temozolomide is also marketed for the treatment of refractory anaplastic astrocytoma patients who have experienced disease progression on a drug regimen containing nitrosourea and procarbazine. Temozolomide is currently available in the form of oral capsules and a vial for injection.

A typical regimen for patients with GBM taking temolozomide consists of two phases, a concomitant phase followed by a maintenance phase, both of which are weight-based dosing regimens. During the concomitant phase, the patient receives an oral administration of 75 mg/m$^2$ of temolozomide daily for 42 days concomitant with focal radiotherapy (60 Gy administered in 30 fractions). This corresponds to approximately 140 mg for a patient having a body surface area (BSA) between 1.8 and 1.9 m$^2$. Four weeks after completing the concomitant phase, the patient receives 6 cycles of maintenance treatment. In the first maintenance cycle, temozolomide is administered at 150 mg/m$^2$ (approximately 280 mg for a patient having a BSA between 1.8 and 1.9 m$^2$) once daily for five days followed by 23 days without treatment. The dosage may be escalated to 200 mg/m$^2$ (approximately 360 mg for a patient having a BSA between 1.8 and 1.9 m$^2$) for the first 5 days of each subsequent cycle. Weight-based dosing using oral tablets and capsules is complex, and inadvertent overdose can be fatal. Capsules and tablets only come in discrete amounts, often requiring patients to self-administer various combinations of different dosage strengths of a medicine to obtain the desired dose. Temodar capsules, for instance, are available in six dosage strengths (5, 20, 100, 140, 180 and 250 mg). In many circumstances, doctors have to round the dose to fit the capsule strengths available. These factors result in a high risk for dispensing errors and administration errors, which have resulted in deaths in the past. One study found that 47% of medication errors were patient and care-giver administration errors, while 29% were dispensing errors. See, e.g., Letarte et al., J. Neurooncol., 120(1), 111-1155, 2014 (analyzing reported medication errors involving oral capsules of temozolomide).

Many weight-based dosed medications avoid the need to combine various dosage strengths of a medicine by providing them as oral or intravenous liquids. Intravenous liquids are inconvenient and undesirable for self-administration. Oral liquid forms of temozolomide are undesirable as temozolomide is dangerous on skin contact, being classified for both skin corrosion/irritation and eye irritation in category 2. In view of these safety issues, the prescribing information for Temodar provides that Temodar capsules are to be swallowed whole, and not chewed, opened, or split. The prescribing information further provides that if Temodar capsules are accidentally opened or damaged, the user should be careful not to inhale the powder from the capsules or get the powder on his or her skin or mucous membranes (for example, nose or mouth). If contact with any of these areas happens, the user is to flush the area with water. There is therefore a need for convenient, safe, and reliable methods for titrating and dosing of temozolomide.

SUMMARY OF THE INVENTION

The term non-liquid medicine as herein is intended to disclose a medicine of any type for treatment of any pathology, condition, symptom, disease, ailment, etc., and that is primarily non-liquid, and that may be administered with or without the addition of a liquid. Exemplary, non-limiting non-liquid medicines are a solid pharmaceutical composition and temozolomide powder in accordance with embodiments of the present invention.

The present invention is directed to a device for dosing and dispensing a dose of a non-liquid medicine. In accordance with embodiments of the present invention, the device comprises a body connectable to a container containing an amount of the non-liquid medicine. When the body is connected with the container, an amount of the non-liquid medicine may be transferred from the container to at least one chamber defined within the body. In a preferred embodiment, two chambers are defined within the body, each having a different predetermined size (i.e., volume). A user may set the amount of the non-liquid medicine to be transferred using a plunger rod slideably located within the at least one chamber, or with each of the two chambers.

A device in accordance with embodiments of the present invention comprises a body comprising a first chamber of a first predetermined size, the body having an outer wall having a first slot defined therethrough. The device further comprises a first plunger rod located in the first chamber and having a first dose tab that extends outside of the first chamber through the first slot. The device still further comprises a coupling connected with the body and being sized and shaped to removably connect the body with the container, the coupling having a first aperture, at least one of the coupling and the body being rotatable between a first position, in which the first aperture is at least partially aligned with the first chamber, and a second position, in which the first aperture is not aligned with the first chamber.

In a device in accordance with embodiments of the present invention, the body further comprises a second chamber of a second predetermined size, the body having a second slot defined through the outer wall. The device still further comprises a second plunger rod located in the second chamber and having a second dose tab that extends outside of the second chamber through the second slot. The coupling further comprises a second aperture, at least one of the coupling and the body being rotatable between a first position, in which at least one of the first aperture and second aperture is at least partially aligned with one of the first chamber and second chamber, and a second position, in which at least one of the first aperture and second aperture is not aligned with one of the first chamber and second chamber.

In a device in accordance with embodiments of the present invention, the first plunger rod is located in, and does not extend out of the body, and the second plunger rod is located in, and does not extend out of the body.

In a device in accordance with embodiments of the present invention, the first predetermined size that is larger than the second predetermine size.

In a device in accordance with embodiments of the present invention, the first plunger rod has a longitudinal axis, and the first dose tab is parallel to, but not coaxial with the longitudinal axis. And the second plunger rod has a longitudinal axis, and the second dose tab is parallel to, but not coaxial with the longitudinal axis.

In a device in accordance with embodiments of the present invention, the first plunger rod is moveable within the first chamber over a movement range, and the first dose tab is accessible by a user over the movement range, and the second plunger rod is moveable within the second chamber over a movement range, and the second dose tab is accessible by a user over the movement range.

In a device in accordance with embodiments of the present invention, the first dose tab is useable by a user to move the first plunger rod in two directions in the first chamber, and the second dose tab is useable by a user to move the second plunger rod in two directions in the second chamber.

In a device in accordance with embodiments of the present invention, the first plunger rod has a longitudinal axis, and the first dose tab is parallel to, but not coaxial with the longitudinal axis, and the first plunger rod is moveable within the first chamber by force applied to the first dose tab in a direction at least partially transverse to the longitudinal axis.

In a device in accordance with embodiments of the present invention, the second plunger rod has a longitudinal axis, and the second dose tab is parallel to, but not coaxial with the longitudinal axis, and the second plunger rod is moveable within the second chamber by force applied to the second dose tab in a direction at least partially transverse to the longitudinal axis.

The present invention is further directed to a kit comprising a device for dosing and dispensing a dose of a non-liquid medicine contained in a container. The non-liquid medicine may be a solid pharmaceutical composition or a temozolomide powder. In accordance with embodiments of the present invention, the device comprises a body comprising a first chamber of a first predetermined size, the body having an outer wall having a first slot defined therethrough. The device further comprises a first plunger rod located in the first chamber and having a first dose tab that extends outside of the first chamber through the first slot. The device still further comprises a coupling connected with the body and being sized and shaped to removably connect the body with the container, the coupling having a first aperture, at least one of the coupling and the body being rotatable between a first position, in which the first aperture is at least partially aligned with the first chamber, and a second position, in which the first aperture is not aligned with the first chamber. In accordance with embodiments of the present invention, the kit further comprises a non-liquid medicine that is readily dispersible in an aqueous solution suitable for oral administration.

The non-liquid medicine of the present invention is preferably a formulation that can be titrated readily and accurately. The formulation has good and consistent flowability, good taste, and good dissolution in acidic medium. Furthermore, the formulation does not readily clump.

One embodiment non-liquid medicine is a solid pharmaceutical composition that is readily dispersible in an aqueous solution suitable for oral administration. The composition comprises:

(a) granules of temozolomide and one or more emulsifiers, the granules coated with a pH dependent coating composition comprising a pH dependent coating material; and (b) a dispersant, wherein at least 80% of the solid pharmaceutical composition dissolves within 30 minutes when tested according to USP I dissolution test (basket) in 900 mL of 0.1 N HCl at 37° C. 0.5° C. and a speed of 100 rpm. The granules may further comprise an adsorbent. The coating composition may also further comprise one or more of glidants, plasticizers, or any combination of any of the foregoing. The composition may further comprise (as extragranular components) one or more of sweeteners, glidants, lubricants, flavors, or any combination of any of the foregoing.

The emulsifiers are selected from sodium lauryl sulfate, poloxamer, saturated polyglycolized glyceride, labrasol, polysorbates, sorbitan esters, cremophor PEG-60 hydrogenated castor oil, PEG-40 hydrogenated castor oil, sodium lauryl glutamate, disodium cocoamphodiacetate, Tyloxapol, Labrafil M2130CS, Labrafil M1944CS, Labrafil M2125CS, Capryol 90, Capryol PGMC, Lauroglycol 90, Lauroglycol FCC, Plurol Oleique CC 497, Labrafac Lipophile WL 1349, Labrafac PG, Transcutol, Compritol HD5 ATO, Compritol 888 Pellets, Biogapress Vegetal BM297ATO, Compritol E ATO, Geloil SC, Transcutol V, Triton X-100, and sodium deoxycholate. Preferably, the emulsifier is stearoyl macrogol-32 glycerides.

The weight ratio of temozolomide and emulsifier is from about 1:1 to about 3:1, and from about 1.5:1 to about 2:1.

The granules further comprise an adsorbent, wherein the adsorbent is preferably colloidal silicon dioxide.

When the pharmaceutical composition is in the form of a powder, the powder has a Hausner ratio of from about 1.00 to about 1.18, and from about 1.00 to about 1.11. The powder has a Carr index of less than 10, and of less than 8, and of less than 6. The powder has a $d_{50}$ of no more than 420 microns, and a $d_{50}$ of no more than 400 microns, and a $d_{90}$ of no more than 600 microns, and a $d_{10}$ of no more than 200 microns. The powder has a bulk density ranging from 0.54 to 0.75 g/cc as measured by USP <616>. The powder has a tap density ranging from 0.59 to 0.80 g/cc as measured by USP <616>.

The pH dependent coating is released at a pH below about 5, and at a pH below about 4.5, and at a pH below about 4. The pH dependent coating material is porous to water. The pH dependent coating material comprises an amino methacrylate copolymer. The pH dependent coating composition further comprises a glidant and a plasticizer.

At least 80% of the solid pharmaceutical composition dissolves within 30 minutes when tested according to USP I dissolution test (basket) in 900 mL of water at 37° C.±0.5° C. and a speed of 100 rpm. At least 80% of the solid pharmaceutical composition dissolves within 30 minutes when tested according to USP I dissolution test (basket) in 900 mL of acetate buffer at a pH of 4.5 at 37° C.±0.5° C. and a speed of 100 rpm. At least 80% of the solid pharmaceutical composition dissolves within 30 minutes when tested according to USP I dissolution test (basket) in 900 mL of phosphate buffer at a pH of 6.8 at 37° C.±0.5° C. and a speed of 100 rpm.

Another embodiment of non-liquid medicine is a temozolomide powder that is readily dispersible in an aqueous medium. The powder comprises:

(a) granules comprising (i) from about 50% to about 75% by weight of temozolimide, (ii) from about 25% to about 50% by weight of emulsifier, and (iii) optionally, from about 0.1% to about 2.5% of adsorbent, where the weight percentages are based on the total weight of the uncoated granules;

(b) a coating composition on the granules comprising (i) from about 40% to about 80% by weight of a pH dependent coating material, (ii) from about 20% to about 60% by weight of glidant, and (iii) from about 0.1% to about 8% by weight of plasticizer, where the weight percentages for the coating composition are based on the total weight of the coating composition;

(c) from about 50% to about 75% by weight of dispersant, based on the total weight of the powder; and (d) optionally, one or more of sweeteners, glidants, lubricants, flavors, or any combination of any of the foregoing based upon 100% total weight of the temozolimide powder.

Yet another embodiment is a method of preparing a solid pharmaceutical composition of temozolomide that is readily dispersible in an aqueous solution suitable for oral administration. The method comprises:

(a) preparing granules of temozolomide and one or more emulsifiers, (b) coating the granules coated with a pH dependent coating composition comprising a pH dependent coating material; and (c) mixing the coated granules with a dispersant and optionally other excipients, wherein at least 80% of the solid pharmaceutical composition dissolves within 30 minutes when tested according to USP I dissolution test (basket) in 900 mL of 0.1 N HCl at 37° C. 0.5° C. and a speed of 100 rpm. In a preferred embodiment, step (b) includes drying the coating for a sufficient time and at a sufficient temperature to render the coating porous to water. In a preferred embodiment, step (b) further includes drying the coated granules for a sufficient time and at a sufficient temperature to render the coating porous to water. For example, the coated granules can be dried at about 25° to about 40° C., such as about 30° to about 40° C. or at about 40° C., for about 5 to about 10 minutes, to remove any residual solvent from the coating and cause cracks or pores to form in the coating. The granules in step (a) may further comprise an adsorbent. The coating composition in step (b) may further comprise one or more of glidants, plasticizers, or any combination of any of the foregoing. Step (c) may further include mixing with the coated granules one or more of sweeteners, glidants, lubricants, flavors, or any combination of any of the foregoing.

Yet another embodiment is a method of treating a proliferative disorder in a patient by administering to the patient a solid pharmaceutical composition or temozolomide powder of the present invention. The proliferative disorder can be, for example, a glioma, melanoma, a lung cancer, a lymphoma, a head and neck cancer, ovarian cancer, colorectal and/or colon cancer or esophageal cancer, or other solid tumor or hematologic malignancy. In one embodiment, the proliferative disorder is GBM. In one embodiment, an effective amount of the solid pharmaceutical composition or temozolomide powder is orally administered to treat the proliferative disorder. The desired amount to be administered may be determined by the use of a measuring device, such as a measuring cup or measuring spoon. The solid pharmaceutical composition or temozolomide powder may be administered concomitantly with radiotherapy.

BRIEF DESCRIPTION OF THE DRAWINGS

Embodiments of the present invention will now be described with reference to the following figures, wherein.

DETAILED DESCRIPTION OF THE INVENTION

The present invention will next be discussed in detail, with reference to the figures. The following describes exemplary embodiments of the present invention. It should be apparent to those skilled in the art that the described embodiments of the present invention are illustrative only and not limiting, being presented by way of example only. All features disclosed in this description may be replaced by alternative features serving the same or similar purpose, unless expressly stated otherwise. Therefore, numerous and various other embodiments are contemplated as falling within the scope and spirit of the present invention.

Device

Figure 1:
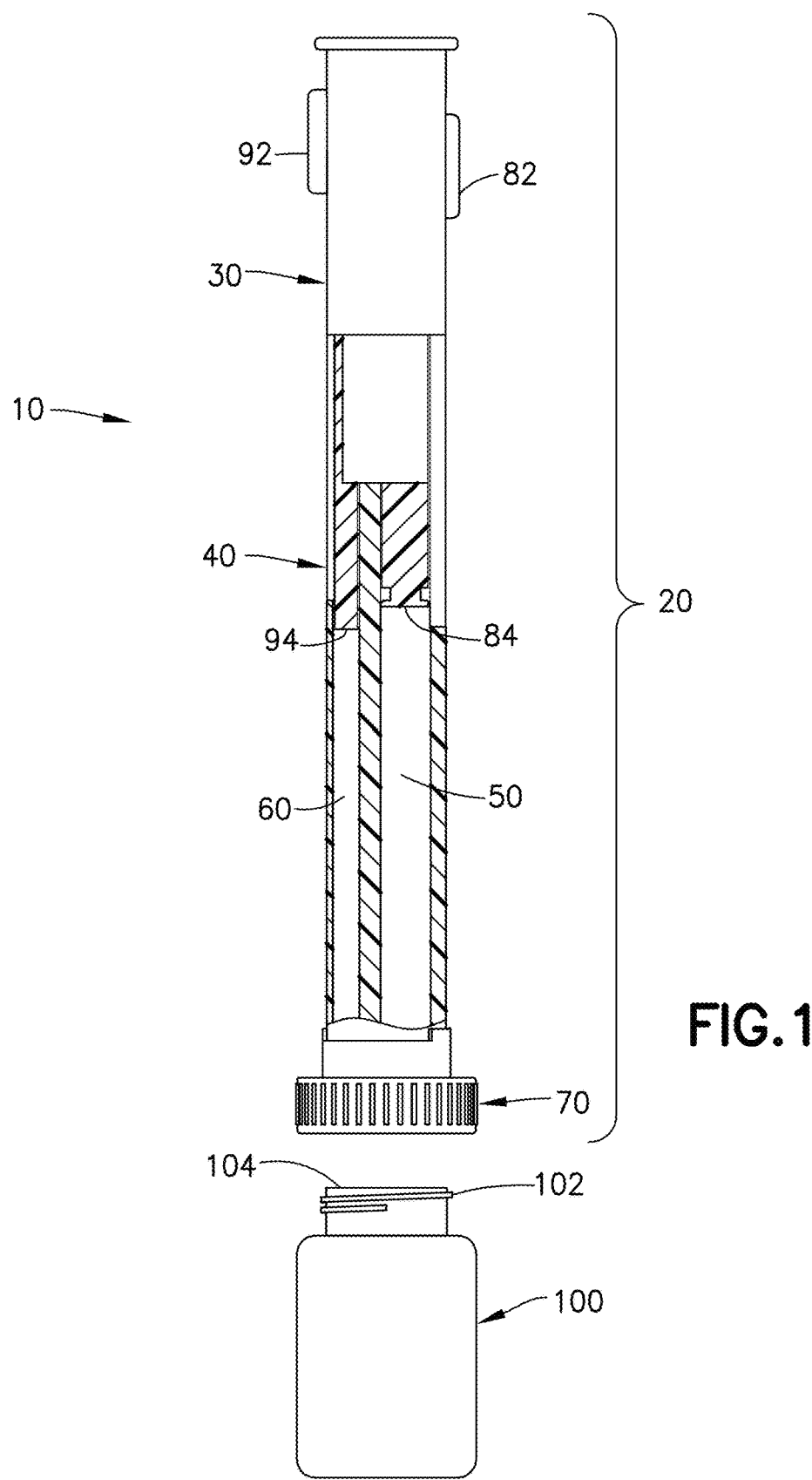
FIG. 1 depicts a partial cut-away front view of a device for dosing and dispensing a dose of non-liquid medicine in accordance with embodiments of the present invention.
Figure 2:
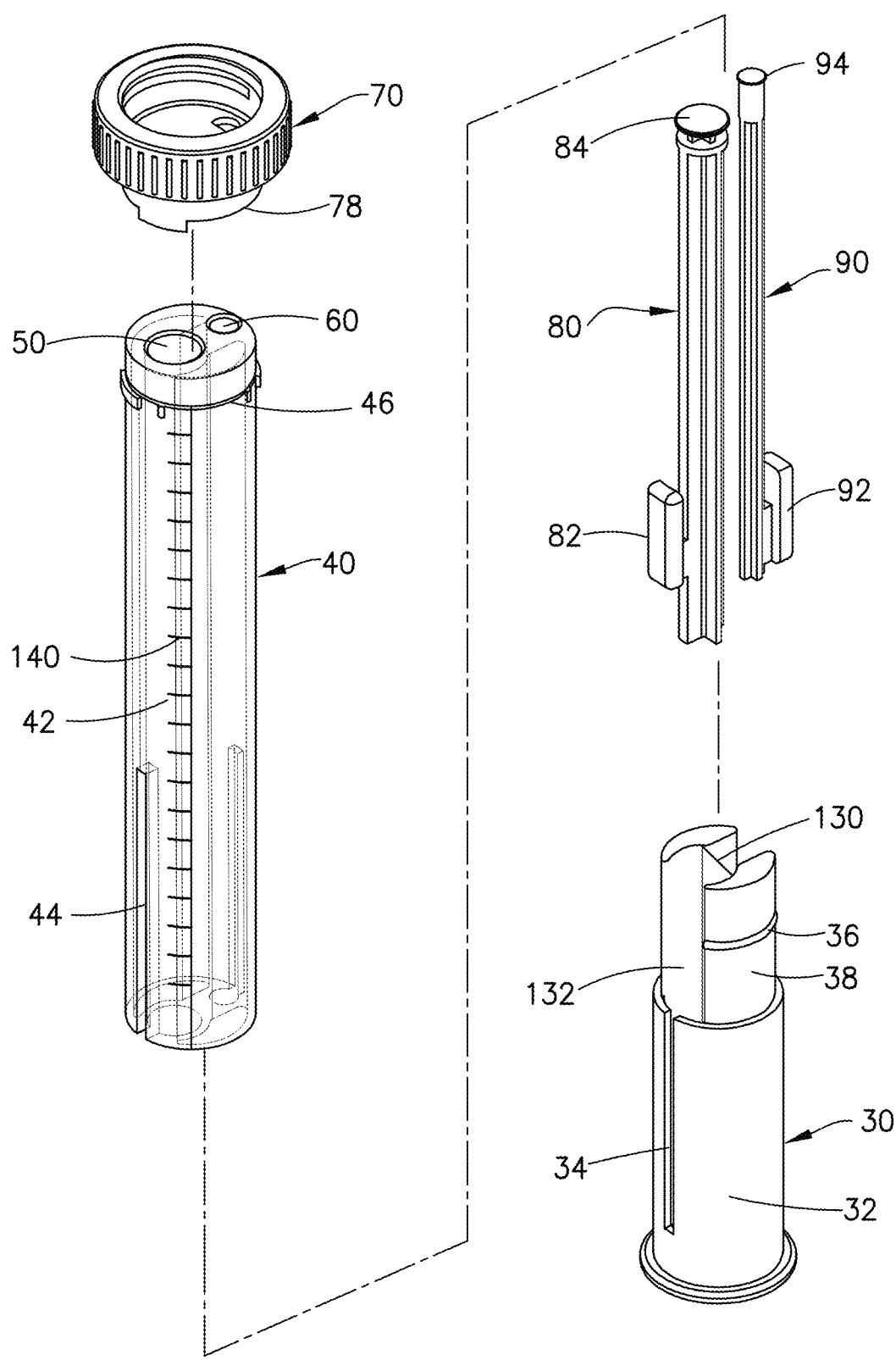
FIG. 2 depicts an exploded view of the device of FIG. 1.

With reference to FIGS. 1 and 2, a device 10 for dosing and dispensing a dose of a non-liquid medicine comprises a body 20 comprised of an upper body 30 and a lower body 40, and a coupling 70 connected with the lower body 40. The device 10 further comprises plunger rods 80, 90 moveably disposed within the body 20, and having dose tabs 82, 92 that extend through an outer wall of the body 20. The upper body 30 and lower body 40 are preferably removably connectable together by complementary parts on the upper body 30 and lower body 40. In a preferred embodiment, a rib 36 is defined on a part of the upper body 30 that engages a complementary feature defined on the lower body 40, such as by way of non-limiting example, a rib or groove (not shown). Each of the upper body 30 and lower body 40 have an outer wall 32, 42 each with a slot 34, 44 defined therethrough. When the upper body 30 and lower body 40 are connected together, the slots 34 and 44 defined a continuous slot in an outer wall of the body 20. Alternatively, only the lower body 40 may have a slot 44 defined through its outer wall 42. First and second chambers 50, 60 are defined in the lower body 40, each having a predetermined volume. In a preferred embodiment, the predetermined volume of chamber 50 ranges from 50 mg to 400 mg, inclusive, and of chamber 60 ranges from 5 mg to 50 mg, inclusive, although other sizes are contemplated by, and within the scope and spirit of the present invention.

Plunger rods 80, 90 are sized and shaped to slidingly fit within one of chambers 50, 60—plunger rod 80 within chamber 50, and plunger rod 90 within chamber 60. Each plunger rod 80, 90 has a dose tab 82, 92 that is usable to move the plunger rod 80, 90 within its respective chamber 50, 60. Movement of the plunger rods 80, 90 in their respective chambers 50, 60 results in a change in volume of the chambers 50, 60, and is how a user of the device 10 sets the desired dose for the non-liquid medicine. Preferably, plunger rods 80, 90 each do not extend out of the body 20. Each plunger rod 80, 90 defines a longitudinal axis, and the dose tabs 82, 92 are parallel to, but not coaxial with the longitudinal axis of the respective plunger rod 80, 90. Preferably, each plunger rod 80, 90 is moveable within its respective chamber 50, 60 over a movement range that positions an end 84, 94 of each plunger rod 80, 90 to vary the size of its respective chamber 50, 60, and set a dose amount in each chamber 50, 60 for the non-liquid medicine. Preferably, the dose tabs 82, 92 are each accessible by a user over the movement range. The dose tabs 82, 92 are also each useable by a user to move the first and second plunger rods 80, 90 in two directions in their respective chambers 50, 60. Thus, a user of the device 10, using the dose tabs 82, 92 to move the plunger rods 80, 90 within the chambers 50, 60, sets a dose amount for the non-liquid medicine. While the plunger rods 80, 90 are located and contained within the first and second chambers 50, 60, the dose tabs 82, 92 extend outside of the first and second chambers 50, 60 through slots 34 and 44 in the upper and lower body 30, 40, or alternatively, through slot 44 in the lower body 40. Movement of the plunger rods 80, 90 is by force applied to the respective dose tab 82, 92 in a direction that is at least partially transverse to the longitudinal axis of the plunger rod, while at the same time applying a force to a dose tab 82, 92 that is at least partially parallel with the longitudinal axis.

Figure 3:
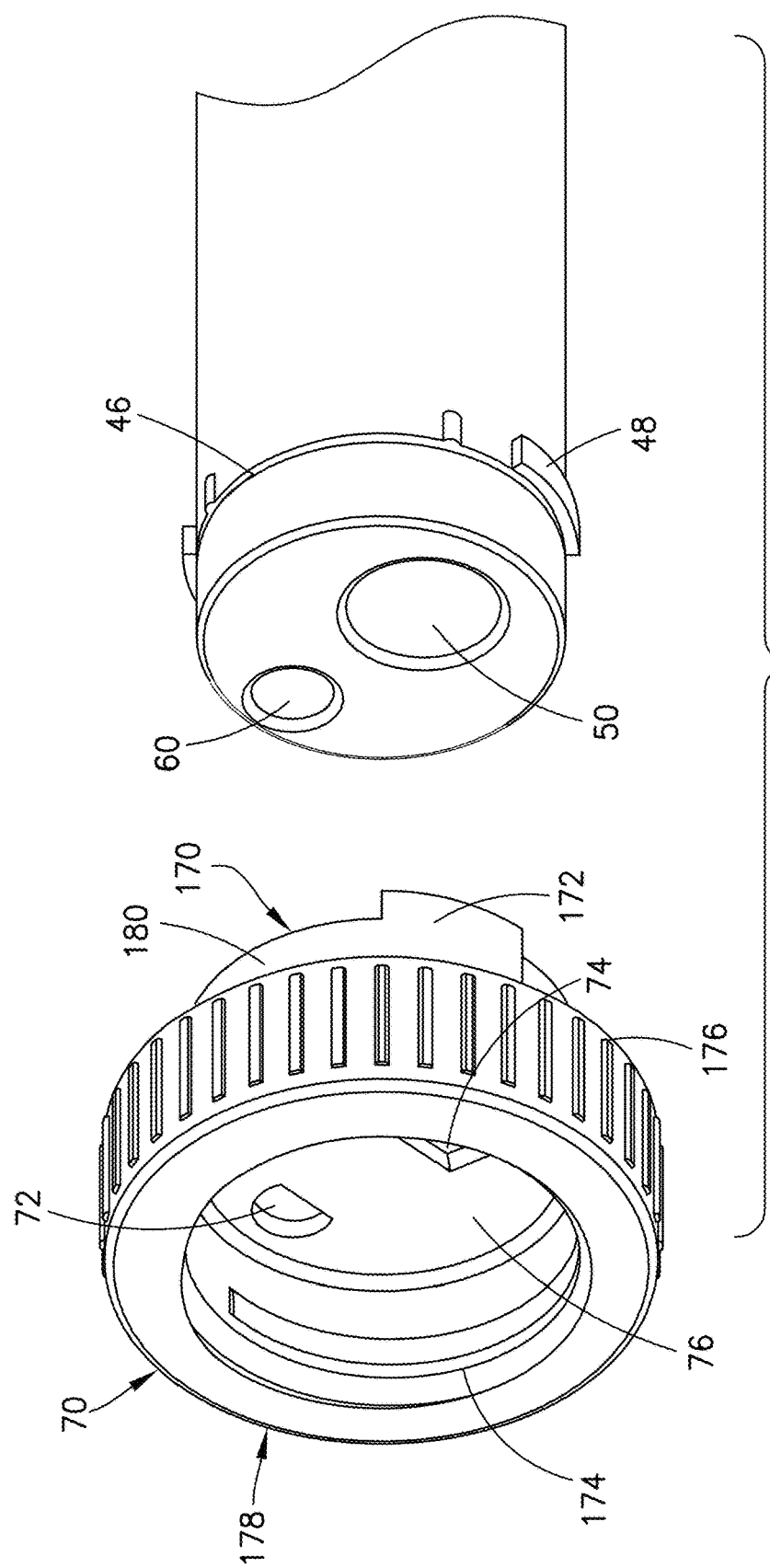
FIG. 3 depicts a detail view of a coupling and lower body of a device for dosing and dispensing a dose of non-liquid medicine in accordance with embodiments of the present invention.
Figure 4:
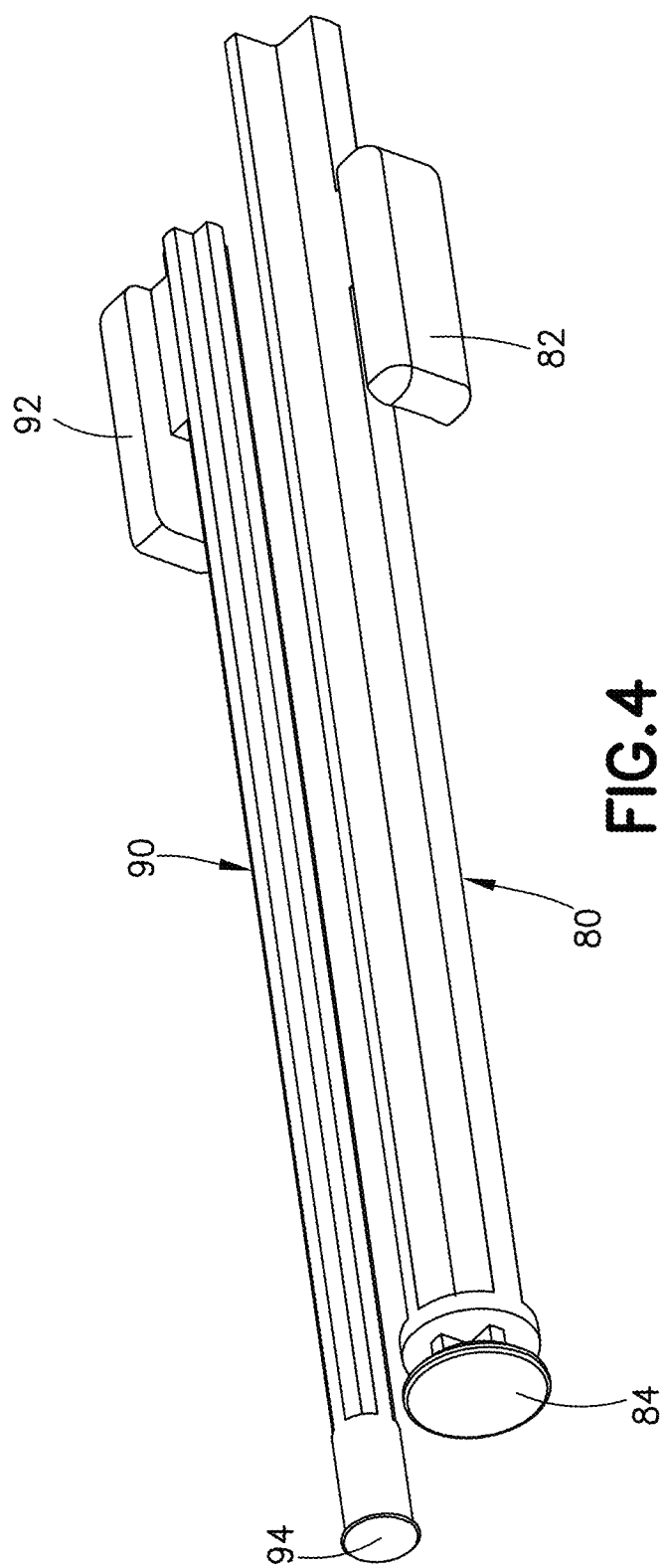
FIG. 4 depicts plunger rods of a device for dosing and dispensing a dose of non-liquid medicine in accordance with embodiments of the present invention.
Figure 5:
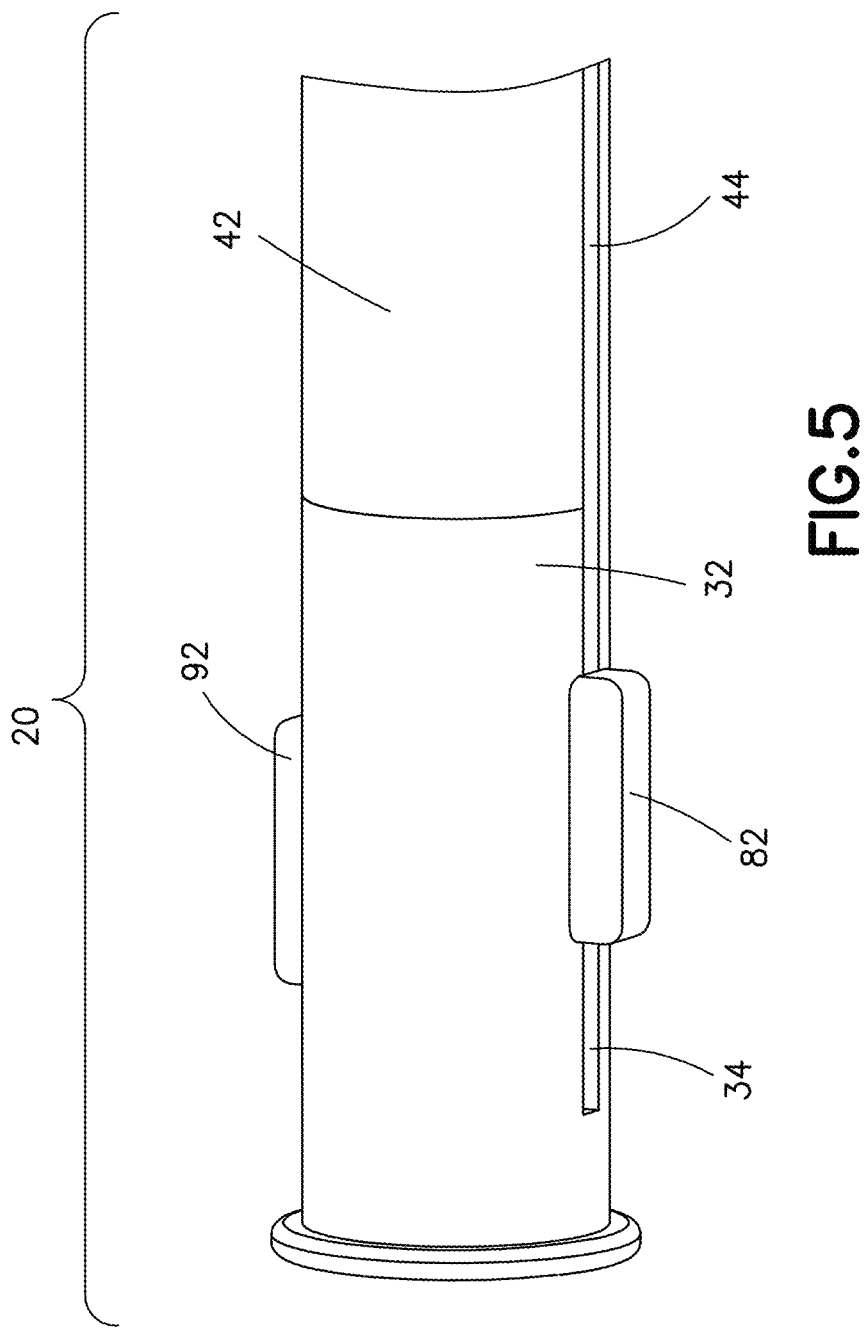
FIG. 5 depicts a detail view of an upper body and partial view of a lower body of a device for dosing and dispensing a dose of non-liquid medicine in accordance with embodiments of the present invention.

With additional reference to FIGS. 3, 4 and 5, one part of the coupling 70 defines a cap 178, and another part defines a collar 170. The cap 178 comprises a top 76, an external grip 176, and an internal threaded part 174 configured to releasably connect the body 20 with the container 100. Alternative configurations of threaded part 174 are also contemplated by, and with the scope and spirit of the present invention, such as, by way of non-limiting example, a bayonet connection, a pressure or friction connection, and other now known or hereafter developed ways to releasably connect the device 10 and container 100. The external grip 176 has a plurality of ribs or other similar structure to facilitate gripping and rotation of the coupling 70 by a user. The coupling 70 has a first aperture 72 and a second aperture 74 defined through the top 76. When connected with the lower body 40, coupling 70 is rotatable to move the apertures 72, 74 into and out of alignment with the first and second chambers 50, 60 respectively. This enables a user to completely or partially open and close the chambers 50, 60, thereby permitting and preventing the non-liquid medicine from moving between the container 100 and chambers 50, 60.

The collar 170 is sized and shaped to receive an end of the lower body 40, and comprises a continuous wall 180 having a tab 172 extending therefrom. The tab 172 engages a stop 48 defined on the outer wall 42 of the lower body 40 when the coupling 70 is connected with the lower body 40. The stop 48 impedes rotational movement of the coupling 70 on the lower body 40. Preferably, two stops 48 are provided on opposite sides of the lower body 40, and two tabs 172 are provided on opposite sides of the collar wall 180.

The coupling 70 is removably and rotatably connectable with the body 20 by complementary features defined in or on the coupling 70 and lower body 40. Preferably, a groove 46 is defined in the outer wall 42 of the lower body 40 that is at least partially circumferential, and that is preferably completely circumferential. The groove 46 is sized and shaped to receive a rib 78 (not shown) defined on an inner surface of the collar 170. The rib 78 may be continuous or it may comprise a plurality of ribs.

In a preferred embodiment, the coupling 70 and body 20 are rotatable with respect to each other to move the first and second apertures 72, 74 into, between, and out of alignment with the first and second chambers 50, 60. With the coupling 70 in a first position, the first aperture 72 and second aperture 74 are respectively aligned with the first chamber 50 and second chamber 60. In the first position, the apertures 72, 74 each provide a maximum opening of the first and second chambers 50, 60, for a maximum amount of non-liquid medicine to move between the container 100 and chambers 50, 60. With the coupling 70 in a second position, the first aperture 72 and second aperture 74 are not aligned with the first chamber 50 and second chamber 60, respectively. In the second position, the first and second chambers 50, 60 are closed, and no non-liquid medicine can move between the container 100 and chambers 50, 60. Thus, with the coupling 70 in the second position, any non-liquid medicine container within the first chamber 50, second chamber 60, and container 100, will remain there. The first and second apertures 72, 74 may be in any position between the first and second position, as determined by the user, to enable more or less non-liquid medicine to pass between the chambers 50, 60 and container 100. Indicia (not shown) may be provided on one or both of the tabs 172 and stops 48 to indicate whether the coupling 70 is in the first or second position, i.e., whether the apertures 72, 74 are opened or closed.

In a preferred embodiment, the various parts of the device 10 of the present invention may be disassembled from each other, as depicted in FIG. 2, to facilitate periodic cleaning of the device 10. Thus, the connections between and among the various parts are not permanent. Alternatively, some or all of the parts of the device 10 of the present invention may be permanently connected together and may not be disassembled.

The upper body 30 has an outer surface 32 having a slot 34 defined therethrough. A non-continuous collar 38 defines a circumference smaller than a circumference defined by the outer surface 32, and is sized and shaped to be received within the lower body 40. With the chambers 50, 60 having different sizes, the upper body 30 is keyed for aligned connection to the lower body 40. In a preferred embodiment, a transverse wall 130 asymmetrically divides an inner cavity 132 of the upper body 30. Transverse wall 130 fits within, and is guided by a gap (not shown) defined between chamber 50 and chamber 60. Alternatively, a guide feature may be defined by upper body 30 that is complementarily sized and shaped to facilitate a keyed connection between the upper body 30 and lower body 40.

In use, the device 10 of the present invention is connected with a container 100 of non-liquid medicine by the coupling 70. Preferably, the apertures 72, 74 of the coupling 70 are in a position that is not aligned with chambers 50, 60, thus preventing non-liquid medicine from moving between the container 100 and the chambers 50, 60. Prior to transferring non-liquid medicine from the container 100 to the chambers 50, 60, the user sets a desired dose amount by moving one or both of the plungers 80, 90 using the dose tabs 82, 92. Dose marking indicia 140 on the outer wall 42 provide a guide for the user to position the dose tabs 82, 92 to set the desired dosage. Once the device 10 and container 100 are connected together by the coupling 70 and the dosage is set, the user may cause the apertures 72, 74 to move into partial or complete alignment with chambers 50, 60 by rotating the coupling 70 and body 20 with respect to each other. In a preferred embodiment, the internal threaded part 174 of the coupling 70 threadedly engages an external threaded part 102 of the container 100 to connect the body 20 and container 100. As the body 20 is rotatably connected with the container 100, the internal threaded part 174 will bottom-out on a lip 104 of the container, arresting further rotation between the coupling 70 and the container 100. However, the body 20 is still rotatable with respect to the coupling 70 to cause the apertures 72, 74 to move into and out of alignment with the chambers 50, 60. This further rotational movement between the body 20 and coupling 70 is arrested by the tabs 172 and stops 48.

Having thus set the desired dose, connected the device 10 and container 100, and aligned the apertures 72, 74 with the chambers 50, 60, the user my now cause non-liquid medicine to move from the container 100 into the chambers 50, 60 by turning the container 100 upside down. Once the chambers 50 60 are filled, and with the container 100 still upside down, the user rotates the body 20 and coupling 70 to move the apertures 72, 74 out of alignment with the chambers 50, 60, thereby sealing the container 100 and apertures 50, 60 from each other and preventing further transfer of non-liquid medicine between them.

The presently claimed invention provides a temozolomide formulation that can be titrated readily and accurately. The formulation has good and consistent flowability, good taste, and good dissolution in acidic medium. Furthermore, the formulation does not readily clump.

All references to the U.S. Pharmacopeia are to the 39$^{th}$ edition unless otherwise indicated.

Granules

The granules are prepared by mixing the temozolomide with one or more emulsifiers and optionally one or more adsorbents. Temozolomide is 3,4-dihydro-3-methyl-4-ox-oimidazo [5,1-d]-as-tetrazine-8-carboxamide (see, e.g., U.S. Pat. No. 5,260,291, the entire contents of which are hereby incorporated by reference) and can be prepared by methods known in the art.

Suitable emulsifiers include, but are not limited to, sodium lauryl sulfate, poloxamer, saturated polyglycolized glyceride (so-called Gelucire), labrasol, polysorbates (such as polyoxyethylene sorbitan monolaurate (Tween 20), polyoxyethylene sorbitan monopalmitate (Tween 40), polyoxyethylene sorbitan monostearate (Tween 60) and polyoxyethylene sorbitan monooleate (Tween 80)), sorbitan esters (such as sorbitan monolaurate (Span 20), sorbitan monopalmitate (Span 40), sorbitan monostearate (Span 60), sorbitan monooleate (Span 80), sorbitan trilaurate (Span 25), sorbitan trioleate (Span 85) and sorbitan tristearate (Span 65)), cremophor (e.g., Cremophor EL), PEG-60 hydrogenated castor oil, PEG-40 hydrogenated castor oil, sodium lauryl glutamate, disodium cocoamphodiacetate, tyloxapol, lauroyl macrogol-6 glycerides (Labrafil M213005=lauroyl polyoxyl-6 glycerides), oleoyl macrogol-6 glycerides (Labrafil M1944C5), linoleoyl macrogol-6 glycerides (Labrafil M2125 CS=linoleoyl polyoxyl-6 glycerides), propylene glycol monocaprylate (Capryol 90), propylene glycol monocaprylate (Capryol PGMC), propylene glycol monolaurate (such as type II (Lauroglycol 90) or type I (Lauroglycol FCC)), polyglyceryl-3 dioleate a oleate (Plurol Oleique CC 497), triglycerides medium-chain (e.g., C8 and C10) (such as Labrafac Lipophile WL 1349), propylene glycol dicaprylocaprate (Labrafac PG), diethylene glycol monoethyl ether (Transcutol), behenoyl polyoxyl-8 glycerides or PEGylated glyceryl behenate (Compritol HD5 ATO), glyceryl behenate (Compritol 888 Pellets), glyceryl dipalmitostearate (Biogapress Vegetal BM297ATO), glyceryl behenate E471 (Compritol E ATO), a mixture of (i) refined soybean oil, (ii) glyceryl distearate and (iii) polyglyceryl-3 dioleate (Geloil SC), diethylene glycol monoethyl ether (Transcutol V), octylphenol ethoxylate (Triton X-100), and sodium deoxycholate. A preferred emulsifier is stearoyl macrogol-32 glycerides (available as Gelucire 50/13 from Gattefosse of Paramus, N.J.). In one preferred embodiment, the emulsifier self-emulsifies on contact with an aqueous medium forming a fine dispersion, such as a microemulsion (SMEDDS).

The weight ratio of temozolomide to emulsifier(s) may range from about 1:1 to about 3:1, such as from about 1:1 to about 2:1 or from about 2:1 to about 3:1. In one embodiment, the solid pharmaceutical composition includes (a) from about 5% to about 30% by weight of temozolimide, and (b) from about 5% to about 30% by weight of emulsifier, based upon 100% total weight of the solid pharmaceutical composition.

Suitable adsorbents include, but are not limited to, talc, fumed silica, colloidal silicon dioxide, calcium silicate, microcrystalline cellulose, and aluminum magnesium metasilicate. A preferred adsorbent is colloidal silicon dioxide. In one embodiment, the amount of adsorbent present in the uncoated granules ranges from about 0.5% to 4%, such as from about 1% to about 2%, based upon the weight of the uncoated granules. In another embodiment, the amount of adsorbent present in the uncoated granules ranges from about 0.1% to about 1%, such as from about 0.2% to about 0.8%, based upon 100% total weight of the solid pharmaceutical composition.

In one embodiment, the granules comprise (i) from about 50% to about 75% by weight of temozolimide, (ii) from about 25% to about 50% by weight of emulsifier, and (iii) optionally, from about 0.1% to about 2.5% or 4% of adsorbent, where the weight percentages are based on the total weight of the uncoated granules. In another embodiment, the granules comprise (i) from about 55% to about 70% by weight of temozolimide, (ii) from about 30% to about 45% by weight of emulsifier, and (iii) optionally, from about 0.1% to about 2.5% or 4% of adsorbent, where the weight percentages are based on the total weight of the uncoated granules. In yet another embodiment, the granules comprise about 1% to about 3% by weight of adsorbent, where the weight percentages are based on the total weight of the uncoated granules.

The granules can be prepared by melting the emulsifier (e.g., stearoyl macrogol-32 glycerides) (e.g., at 50° C.), adding the temozolomide and mixing to uniformity while maintaining the heat, allowing the mixture to harden, optionally breaking the mixture into smaller pieces (e.g., using a high shear granulator and then a jet mill), and granulating the mixture, optionally with one or more adsorbents.

Coating

The granules are coated to provide taste masking, safety in case the granules spill, and the desired release profile upon oral administration. In one embodiment, the coating composition includes a pH dependent coating material. The coating composition is preferably porous so the temozolimide can be dissolved in aqueous medium.

The pH dependent coating material dissolves when there is a decrease in pH, and result in the release of the temozolomide. The pH dependent material may be released at a pH below about 6. The pH dependent coating material preferably is released at a pH below about 5. In one embodiment, the pH dependent coating material is released at a pH below about 4.5. In another embodiment, the pH dependent coating material is released at a pH below about 4. Applicants surprisingly discovered that the pH dependent coating dissolves in aqueous medium having a pH greater than 5 (e.g., water), such as water having a pH of about 6.8 to about 7.5. The coating provides a barrier permitting safe handling of the composition and preventing a patient or caregiver from the toxic effects of skin contact of temozolimide in the event of a spill.

Suitable pH dependent coating materials include, but are not limited to, methacrylate-based polymers, such as cationic polymers with a dimethylaminoethyl ammonium group (e.g., Eudragit® E PO available from Evonik Industries of Darmstadt, Germany). A preferred pH dependent coating material is amino methacrylate copolymer (e.g., Eudragit® E 100 available from Evonik Industries of Darmstadt, Germany). The pH dependent coating material can be a pH sensitive cationic coating material, such as polyvinylacetal diethylaminoacetate (AEA), acrylamide, aminoethyl methacrylate, N,N'-dimethylaminomethylacrylamide, N,N'-dimethylaminoethyl methacrylate, N,N'-dimethylaminopropyl methacrylate, N,N'-diethylaminoethyl methacrylate, diallyldimethylammonium chloride, and cationic polymers from natural sources (such as polylysine, polyhistidine, and chitosan).

In one embodiment, the pH dependent coating on the coated granules is porous to water.

Preferably, the amount of the pH dependent coating material is sufficient to result in taste masking of the temozolomide yet result in a desirable dissolution profile. In one embodiment, the pH dependent coating material is present in the coating composition in the range of about 40% to about 80%, and more preferably in a range of about 50% to about 70% by weight of the dry coating. In another embodiment, the pH dependent coating material is present in the range of about 1% to about 10%, and more preferably in a range of about 2.5% to about 8% or about 2.5% to about 5% by weight of the solid pharmaceutical composition A coating solution can be prepared by dissolving the pH dependent coating material in a solvent, such as isopropanol, acetone, or a mixture thereof. Optionally, additional excipients, such as a glidant (such as talc) and plasticizer (such as PEG 6000), can be added to the coating solution.

Suitable glidants include, but are not limited to, talc, fumed silica, colloidal silicon dioxide, magnesium stearate, stearic acid, kaolin, and magnesium trisilicate. A preferred glidant for the coating composition is talc. In one embodiment, the glidant is present in the coating composition in the range of about 20% to about 60% by weight, where the weight percentages are based on the total weight of the (dry) coating composition. In another embodiment, the glidant is present in the coating composition in the range of about 5% to about 40%, and more preferably in a range of about 25% to about 35% by weight of the dry coating. In yet another embodiment, the glidant is present in the range of about 0.5% to about 5%, and more preferably in a range of about 1% to about 2% by weight of the solid pharmaceutical composition.

Suitable plasticizers include, but are not limited to, polyethylene glycol, propylene glycol, triacetin, liquid paraffin, diethyl phthalate, dibutyl phthalate, glycerin, lecithin, triethyl citrate, fractionated coconut oil, castor oil, and polysorbate 80. A preferred plasticizer is polyethylene glycol (PEG), for example, PEG having a molecular weight ranging from 1000 to 8000, such as PEG 6000. In one embodiment, the plasticizer is present in a range of about 0.1% to about 8%, more preferably in a range of about 1% to about 8% by weight, where the weight percentages are based on the total weight of the (dry) coating composition. In another embodiment, the plasticizer is present in a range of about 1% to about 10%, more preferably in a range of about 3% to about 8% by weight of the dry coating. In yet another embodiment, the plasticizer is present in the range of about 0.1% to about 0.8%, and more preferably in a range of about 0.2% to about 0.4% by weight of the solid pharmaceutical composition.

The coating composition can be sprayed onto the temozolomide granules, for example, using a fluidized bed granulator (using, for example, a top spray). Preferably, the spraying is performed at a temperature of about 25° to about 40° C. In one embodiment, the spray coating is performed in a fluidized bed granulator for about 0.5 to about 4 hours, such as from about 1 to about 3 hours. Preferably, the coated granules are subsequently dried for a sufficient time to remove any residual solvents and render the coating porous to water. In one embodiment, the granules are dried at about 25° to about 40° C. (such as from about 30° to about 40° C. or at about 40° C.) for about 5 to about 10 minutes (or until the solvents have been removed to specified levels). In another embodiment, the coated granules are dried until their temperature raises by about 5° to about 10° C. (such as to a temperature ranging from about 32° to about 40° C., such as from about 33° to about 38° C. (for example, as measured by a thermometer in the bottom bowl of a fluidized bed granulator (where the top spray is off during drying)). Without wishing to be bound by any particular theory, the inventors theorize that the drying step results in cracks in the coating permitting it to dissolve in water, even at an elevated pH such as pH 6.8.

Dispersant and Other Components

The final solid pharmaceutical preparation can be prepared by mixing the coated granules with one or more dispersants and optionally other components, such as sweeteners, glidants, lubricants, and flavors.

Suitable dispersants include, but are not limited to, crospovidone, Pharmasperse® 416, isomalt, maltodextrin, mannitol, maltose, sorbitol, and maltitol. One preferred dispersant is Pharmasperse® 416 (available from SPI Pharma, Inc. of Wilmington, Del.), which contains 49.3%-69.3% polyol (on a dry basis) and 30.4%-50.4% calcium carbonate and has a tapped density of 0.59-0.75 g/mL and a bulk density of 0.52-0.68 g/mL. In one embodiment, the amount of dispersant ranges from about 40% to about 80%, based upon the total weight of the solid pharmaceutical composition. In another embodiment, the amount of dispersant ranges from about 50% to about 75%, such as from about 60% to about 65%, based upon the total weight of the solid pharmaceutical composition.

Suitable sweeteners include, but are not limited to, sucralose, sodium saccharin, aspartame, and neutrame. The amount of sweeteners can range from about 0% to about 2%, such from about 0.1% to about 0.5%, based upon the total weight of the solid pharmaceutical composition.

Suitable glidants include, but are not limited to, talc, fumed silica, colloidal silicon dioxide, magnesium stearate, stearic acid, kaolin, and magnesium trisilicate. In one embodiment, the glidant is colloidal silicon dioxide. In one embodiment, the amount of glidant (extragranular) ranges from about 0.1% to about 2%, such as from about 0.2% to about 1%, based upon the total weight of the solid pharmaceutical composition.

Suitable lubricants include, but are not limited to, magnesium stearate. The amount of lubricants can range from about 0.1% to about 1%, such from about 0.2% to about 0.5%, based upon the total weight of the solid pharmaceutical composition.

Suitable flavors include natural and artificial powdered flavors. The amount of flavors can range from about 0% to about 4%, such from about 1% to about 3%, based upon the total weight of the solid pharmaceutical composition.

Solid Pharmaceutical Composition

In one preferred embodiment, the solid pharmaceutical composition is in the form of a powder.

In one preferred embodiment, the powder has a Hausner ratio of from about 1.00 to about 1.18, such as from about 1.00 to about 1.11.

In another preferred embodiment, the powder has a Carr index of less than 10, such as less than 8 or less than 6 (e.g., from about 3 to about 7 or from about 4 to about 6).

In yet another preferred embodiment, the powder has a Hausner ratio of from about 1.00 to about 1.18 and a Carr index of less than 8. In yet another preferred embodiment, the powder has a Hausner ratio of from about 1.00 to about 1.11 and a Carr index of less than 6 (e.g., from about 3 to about 7 or from about 4 to about 6).

In one embodiment, the powder has a $d_{50}$ of no more than 420 microns, such as no more than 400 microns. Particle size distribution measurements, such as $d_{10}$, $d_{50}$, and $d_{90}$ values are measured according to U.S. Pharmacopeia <429>(39$^{th}$ edition), for example, ising a Malvern Masterizer 2000 using a Scirocco 2000 accessory (available from Malvern Instruments Ltd. Of Malvern, Worcestershire, UK).

In one embodiment, the powder has a $d_{90}$ of no more than 600 microns, such as a $d_{90}$ of no more than 500 microns. For instance, the $d_{90}$ may range from about 300 to about 600 microns, such as from about 400 to about 550 microns In one embodiment, the powder has a $d_{10}$ of no more than 200 microns, such as a $d_{10}$ of no more than 150 microns, a $d_{10}$ of no more than 100 microns, a $d_{10}$ of no more than 75 microns, or a $d_{10}$ of no more than 50 microns. For instance, the $d_{10}$ may range from about 5 to about 200 microns, such as from about 10 to about 100 microns, or from about 10 to about 75 microns.

In one embodiment, no more than 10% of the powder has a particle size less than 50 microns. For example, in one embodiment, no more than 10% of the powder has a $d_{10}$ less than 50 microns. In another embodiment, no more than 10% of the powder has $d_{50}$ less than 50 microns.

In a preferred embodiment, the powder has a bulk density ranging from about 0.5 to about 0.75 g/cc or from about 0.54 to about 0.75 g/cc as measured by USP <616>.

In another preferred embodiment, the powder has a tap density ranging from about 0.6 to about 0.8 g/cc or from about 0.59 to about 0.80 g/cc as measured by USP <616>.

In one embodiment, at least 80% of the composition dissolves within 30 minutes when tested according to USP I dissolution test (basket) in 900 mL of 0.1 N HCl at 37° C.±0.5° C. and a speed of 100 rpm. In another embodiment, at least 90%, 95%, 98%, or 99% of the composition dissolves within 30 minutes when tested according to USP I dissolution test (basket) in 900 mL of 0.1 N HCl at 37° C.±0.5° C. and a speed of 100 rpm.

In one embodiment, at least 80% of the composition dissolves within 15 minutes when tested according to USP I dissolution test (basket) in 900 mL of 0.1 N HCl at 37° C.±0.5° C. and a speed of 100 rpm. In another embodiment, at least 90%, 95%, 98%, or 99% of the composition dissolves within 15 minutes when tested according to USP I dissolution test (basket) in 900 mL of 0.1 N HCl at 37° C.±0.5° C. and a speed of 100 rpm.

In one embodiment, at least 80% of the composition dissolves within 30 minutes when tested according to USP I dissolution test (basket) in 900 mL of water at 37° C.±0.5° C. and a speed of 100 rpm. In another embodiment, at least 90% or 95% of the composition dissolves within 30 minutes when tested according to USP I dissolution test (basket) in 900 mL of water at 37° C.±0.5° C. and a speed of 100 rpm.

In one embodiment, at least 80% of the composition dissolves within 15 minutes when tested according to USP I dissolution test (basket) in 900 mL of water at 37° C.±0.5° C. and a speed of 100 rpm. In another embodiment, at least 90% or 95% of the composition dissolves within 15 minutes when tested according to USP I dissolution test (basket) in 900 mL of water at 37° C.±0.5° C. and a speed of 100 rpm.

In one embodiment, at least 80% of the composition dissolves within 30 minutes when tested according to USP I dissolution test (basket) in 900 mL of acetate buffer at a pH of 4.5 at 37° C.±0.5° C. and a speed of 100 rpm. In another embodiment, at least 90% or 95% of the composition dissolves within 30 minutes when tested according to USP I dissolution test (basket) in 900 mL of acetate buffer at a pH of 4.5 at 37° C.±0.5° C. and a speed of 100 rpm.

In one embodiment, at least 80% of the composition dissolves within 15 minutes when tested according to USP I dissolution test (basket) in 900 mL of acetate buffer at a pH of 4.5 at 37° C.±0.5° C. and a speed of 100 rpm. In another embodiment, at least 90% or 95% of the composition dissolves within 15 minutes when tested according to USP I dissolution test (basket) in 900 mL of acetate buffer at a pH of 4.5 at 37° C.±0.5° C. and a speed of 100 rpm.

In one embodiment, at least 80% of the composition dissolves within 30 minutes when tested according to USP I dissolution test (basket) in 900 mL of phosphate buffer at a pH of 6.8 at 37° C.±0.5° C. and a speed of 100 rpm. In another embodiment, at least 90% or 95% of the composition dissolves within 30 minutes when tested according to USP I dissolution test (basket) in 900 mL of phosphate buffer at a pH of 6.8 at 37° C.±0.5° C. and a speed of 100 rpm.

In one embodiment, at least 80% of the composition dissolves within 15 minutes when tested according to USP I dissolution test (basket) in 900 mL of phosphate buffer at a pH of 6.8 at 37° C.±0.5° C. and a speed of 100 rpm. In another embodiment, at least 90% or 95% of the composition dissolves within 15 minutes when tested according to USP I dissolution test (basket) in 900 mL of phosphate buffer at a pH of 6.8 at 37° C.±0.5° C. and a speed of 100 rpm.

In another embodiment, the total organics content released from the composition according to the Spill Test in Example 3 is less than 200 ppm, more preferably less than 150 ppm, and even more preferably less than 100 ppm.

Uses

The non-liquid medicine of the present invention is preferably a solid pharmaceutical composition or temozolomide powder that can advantageously be directly administered to the patient. The patient may optionally administer the powder with a separate drink of water.

Yet another embodiment is a method of treating a proliferative disorder by administering a solid pharmaceutical composition or temozolomide powder of the present invention. The proliferative disorder can be, for example, a glioma, melanoma, a lung cancer, a lymphoma, a head and neck cancer, ovarian cancer, colorectal and/or colon cancer or esophageal cancer, or other solid tumor or hematologic malignancy. In one embodiment, an effective amount of the solid pharmaceutical composition or temozolomide powder is orally administered to treat the proliferative disorder.

One embodiment is a method of treating a patient having GBM by administering the solid pharmaceutical composition or temozolomide powder of the present invention. A typical regimen for patients with GBM taking temolozomide consists of two phases, a concomitant phase followed by a maintenance phase. During the concomitant phase, the patient receives an oral administration of 75 mg/m² of temolozomide daily for 42 days concomitant with focal radiotherapy (60 Gy administered in 30 fractions). This corresponds to approximately 140 mg for a patient having a body surface area (BSA) between 1.8 and 1.9 m². Four weeks after completing the concomitant phase, the patient receives 6 cycles of maintenance treatment. In the first maintenance cycle, temozolomide is administered at 150 mg/m² (approximately 280 mg for a patient having a BSA between 1.8 and 1.9 m²) once daily for five days followed by 23 days without treatment. The dosage may be escalated to 200 mg/m² (approximately 360 mg for a patient having a BSA between 1.8 and 1.9 ml) for the first 5 days of each subsequent cycle.

The solid pharmaceutical composition or temozolomide powder of the present invention may be administered by measuring an appropriate or desired dose of the solid pharmaceutical composition or temozolomide powder with a measuring device, such as the inventive device 10, and then administering (e.g., by the oral route) the dose.

EXAMPLES

The following examples are merely illustrative of the present invention and should not be construed as limiting the scope of the invention in any way as many variations and equivalents that are encompassed by the present invention will become apparent to those skilled in the art upon reading the present disclosure.

Example 1

A powder having the formulation shown in Table 1 below was prepared as follows.

TABLE 1

| Ingredient | % (w/w) | Amount per gram |
| --- | --- | --- |
| Temozolomide | 10.00% | 100.0 mg |
| Pharmasperse 416 | 77.00% | 770.0 mg |
| Gelucire 50/13 (steroyl macrogol-32 glycerides) | 10.00% | 100.0 mg |
| Eudragit E 100 (Dimethylaminoethyl Methacrylate Copolymer) | 2.00% | 20.0 mg |
| Talc, NF | 0.85% | 8.5 mg |
| PEG 6000 | 0.15% | 1.5 mg |

The Gelucire 50/13 was heated to approximately 50° C. until liquefied. Temozolomide was added at a 1:1 ratio to the melted Gelucire. The mixture was mixed until the temozolomide was uniformly dispersed while maintaining heating at approximately 50° C. The heated dispersion was transferred to a foil-lined tray, and allowed to cool and harden. The hardened sheets of the mixture were broken apart into smaller pieces. The hardened pieces were milled using a Sturtevant SDM-2 model jet mill to a target particle size of 40 μm-80 μm or an average of 60 μm.

A coating mixture was prepared by (i) dissolving Eudragit E 100 in a 50/50 (by weight) mixture of acetone/isopropanol (approximately 12%-15% Eudragit by weight) to form a first mixture, (ii) adding talc and PEG 6000 to a separate 50/50 (by weight) mixture of acetone/isopropanol and mixing vigorously (5%-7% talc by weight; 0.5%-1% PEG 6000 by weight) to form a second mixture, and (iii) combining the first and second mixtures to form the coating mixture. The Eudragit E 100 coating mixture was sprayed onto the temozolomide granules using a fluid bed granulator with top-spray capability until fully coated (approximately 1-10 mg/cm² with a target of 8 mg/cm²). The coated granules were dried and collected. The coated granules were combined with Pharmasperse 416 in a ratio that provides for 100 mg temozolomide per gram of powder.

Example 2

Oral granules (powder) having the formulation shown in Table 2 below was prepared as follows.

The Gelucire 50/13 was heated to approximately 50° C. until liquefied. Temozolomide was added to the melted Gelucire. The mixture was mixed until the temozolomide was uniformly dispersed (approximately 15 minutes) while maintaining heating at approximately 50° C. The heated dispersion was transferred to cooling trays lined with non-stick or wax paper, and allowed to cool and harden. The hardened sheets of the dispersion were broken apart into smaller pieces.

Half of the silicon dioxide was added to a high shear granulator. The hardened pieces of the dispersion were transferred to the high shear granulator. The blend was mixed with both the bottom agitator and chopper blade to reduce the particle size of the Gelucire/temozolomide dispersion and discharged. The material was processed through a jet mill to the desired particle size. The granules were added to a fluid bed coater equipped with top spray capability.

Eudragit E 100 was mixed with a 60/40 mixture of isopropanol/acetone until dissolved. Talc and PEG 6000 were added and mixed until uniform to form a suspension. The Eudragit suspension was sprayed onto the temozolomide granules with a Glatt GPCG 120 fluid bed processor equipped with a top spray (inlet air temperature of 25°-40° C., outlet air temperature of 20°-25° C., atomizing air pressure of 1.5-2 bar) for 2 hours. The spraying was discontinued, and the drying in the fluid bed processor continued for ~8-9 minutes, such that the temperature of the product as measured in the bottom bowl raised by 7°-8° C. (indicating that the solvents had been removed).

The coated granules were added to a V-blender. Pharmasperse 416, sucralose, and flavor were added and mixed for 15-30 minutes. The second half of the colloidal silicon dioxide and magnesium stearate were added and mixed for 2 minutes. The blend was discharged from the V-blender.

TABLE 2

| Ingredient | % (w/w) | Amount per gram |
| --- | --- | --- |
| Temozolomide | 18.0% | 180.0 mg |
| Pharmasperse 416 | 63.9% | 639.15 mg |
| Gelucire 50/13 (stearoyl macrogol-32 glycerides) | 10.0% | 100.0 mg |
| Amino methacrylate copolymer, NF (Eudragit E 100) | 2.85% | 28.5 mg |
| Talc, NF | 1.4% | 14.0 mg |
| PEG 6000, NF | 0.285% | 2.85 mg |
| Magnesium stearate, NF | 0.35% | 3.5 mg |
| Sucralose, NF | 0.2% | 2.0 mg |
| Colloidal silicon dioxide, NF | 1.0% | 10 mg |
| Natural and Artificial Powdered Flavors | 2.0% | 20.0 mg |
| Total | 100% | 1000 mg |

The particle size distribution of the oral granules was determined according to U.S. Pharmacopeia <429>(39th edition) using a Malvern Mastersizer 2000 with a Scirocco 2000 accessory (available from Malvern Instruments Ltd. of Malvern, Worcestershire, UK). The oral granules had a $d_{10}$ of 31.3 microns, a $d_{50}$ of 239.1 microns, and a $d_{90}$ of 484.8 microns.

250 mg of the oral granules were tested by USP dissolution apparatus I (baskets) at 100 rpm in 900 mL of medium at 37° C. The dissolution test was repeated six times and the dissolution percentages averaged for each run. The test results are provided in the table below.

TABLE 3

| Run | Medium | Percentage dissolved after 15 minutes | Percentage dissolved after 30 minutes |
|---|---|---|---|
| #1 | Water only | 90.2% | 99.9% |
| #2 | 0.1N HCl | 88.7% | 100.1% |
| #3 | Acetate, pH 4.5 | 87.3% | 99.9% |
| #4 | Phosphate buffer, pH 6.8 | 88.4% | 100.2% |

Figure 6:
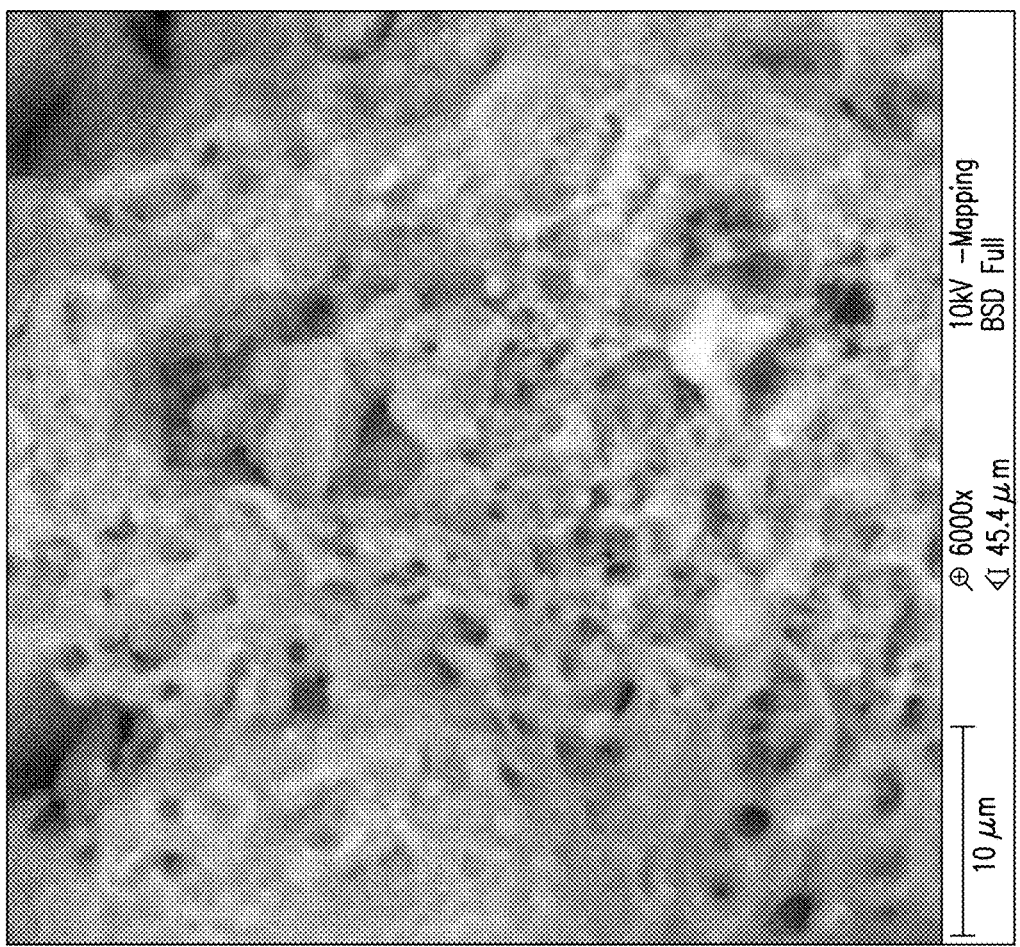
FIGS. 6-8 are scanning electron microscope (SEM) images of the granules of Example 2.
Figure 7:
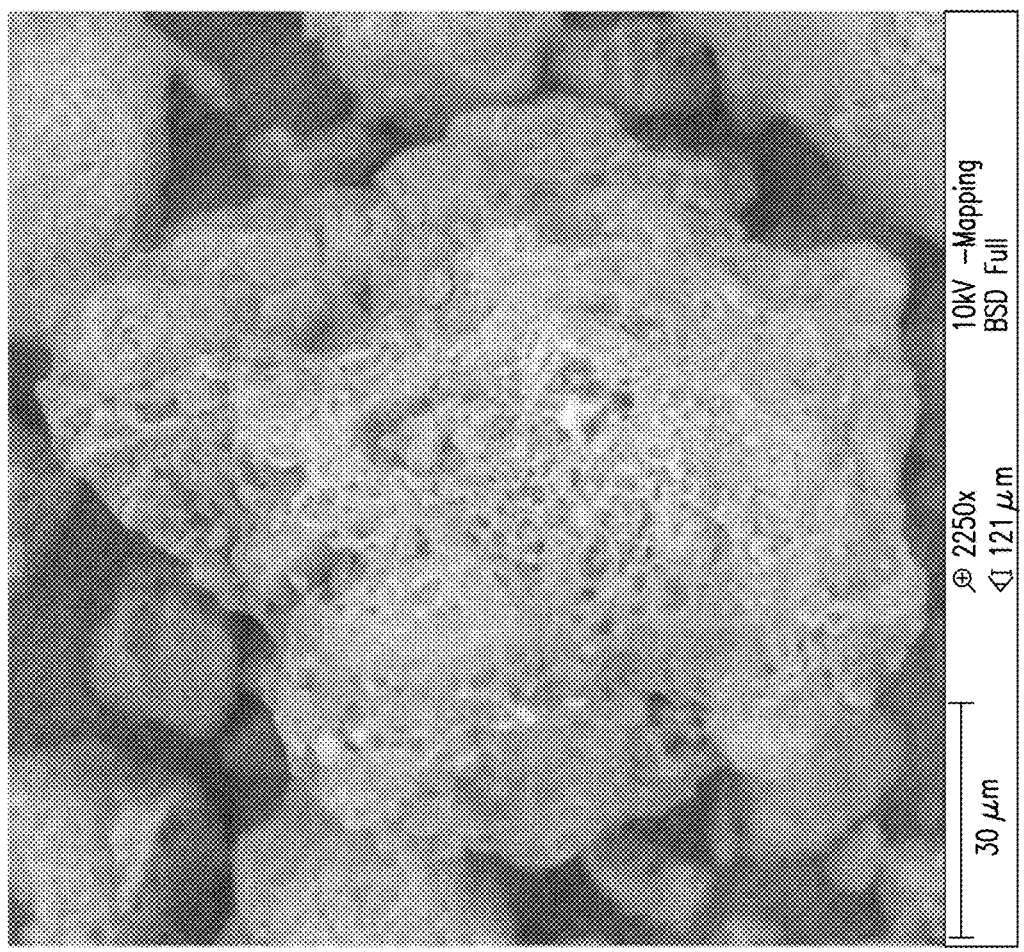
Figure 8:
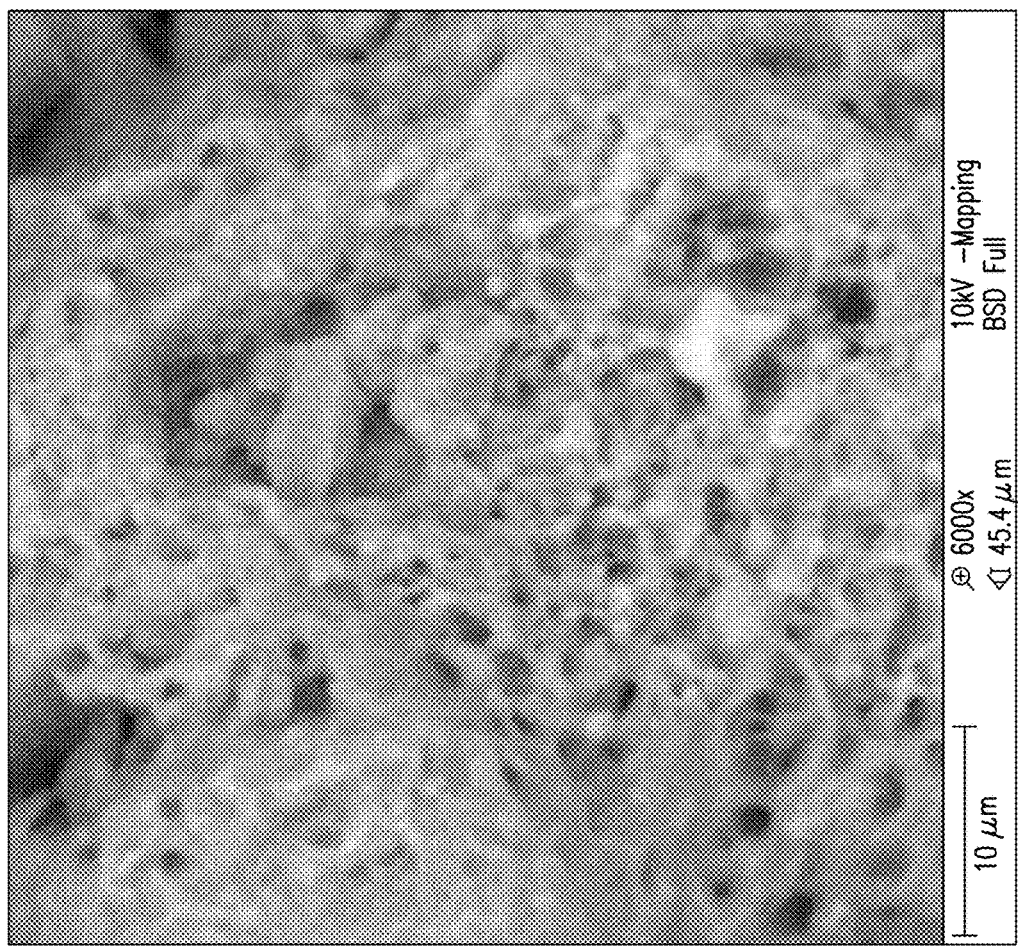

Scanning electron microscope (SEM) images of these granules are provided in FIGS. 6-8. As can be seen from these images, the coated granules have cracks or pores, which the inventors theorize permit the granules to readily dissolve in water (even at an elevated pH such as pH 6.8). At the same time, the coating renders the granules safe for handling and provides taste masking.

Example 3

To discover how much drug material is absorbed upon a potential spill, a Franz Diffusion cell glass apparatus was used to measure the amount of drug material absorbed through a paper towel that is commonly used to clean up spills.

The Spill Test Procedure

The spill test was conducted as follows (herein referred to as the "Spill Test"). Two Franz diffusion cell glass apparatuses were each filled with 2.5 mL of tap water in the collection compartment. For each apparatus, a 1 square inch absorbent towel (the barrier layer) was placed between the Franz diffusion cell and the cell top and clamped together.

The coated granules of Example 2 (Table 2) in an amount equivalent to 250 mg temozolomide was placed in the donor compartment of one Franz diffusion cell and labeled "A" (Test Formulation).

A 250 mg capsule of generic temozolomide was placed in the donor compartment of the other Franz diffusion cell and labeled "B" (Reference Formulation).

The drug material for both diffusion cells A and B remained in contact with the barrier layer for 10 minutes. The water in the collection compartment was then collected and analyzed to determine the total organic carbon content.

Results

The results are shown in Table 4 below. Because the powder of Example 2 meets the same dissolution standard (85% dissolved in water in 10 minutes) as generic temozolomide capsules, similar results in this spill test were expected. Surprisingly, these results show that the coated granules of Example 2 reduce exposure by more than 85% compared to temozolomide powder from generic temozolomide capsules.

TABLE 4

| Formulation | Total Organic Carbon Content |
|---|---|
| Test Formulation "A" | 70.5 ppm |
| Reference Formulation "B" | 515 ppm |

Kit

In an additional preferred embodiment, the present invention comprises kit comprising a device 10 for dosing and dispensing a dose of a non-liquid medicine contained in a container 100, and a non-liquid medicine that is readily dispersible in an aqueous solution suitable for oral administration. The device 10 comprises a body 20 comprising a first chamber 50 of a first predetermined size, the body 230 having an outer wall 42 having a first slot 44 defined therethrough. The device 10 further comprises a first plunger rod 80 located in the first chamber 50 and having a first dose tab 82 that extends outside of the first chamber 50 through the first slot 44. The device 10 still further comprises a coupling 70 connected with the body 20 and being sized and shaped to removably connect the body 20 with the container 100. The coupling has a first aperture 72, at least one of the coupling 70 and the body 20 being rotatable between a first position, in which the first aperture 72 is at least partially aligned with the first chamber 50, and a second position, in which the first aperture 72 is not aligned with the first chamber 50.

Throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Modifications to embodiments of the present invention are possible without departing from the scope of the invention as defined by the accompanying claims. Expressions such as "including," "comprising," "incorporating," "consisting of," "have," "is," used to describe and claim the present invention are intended to be construed in a non-exclusive manner, namely allowing for articles, components or elements not explicitly described herein also to be present. Reference to the singular is to be construed to relate to the plural, where applicable.

Although specific example embodiments have been described, it will be evident that various modifications and changes may be made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Description, therefore, is not to be taken in a limiting sense, and the scope of various embodiments is defined only by the appended claims, along with the full range of equivalents to which such claims are entitled.

What is claimed is:

1. A device for dosing and dispensing a dose of a non-liquid medicine contained in a container, the device comprising:
   a body comprising a first chamber of a first predetermined size and configured to contain the non-liquid medicine, the body having an outer wall, a first part of which is shared with the first chamber, a first slot being defined through the first part of the outer wall of the body shared with the first chamber;
   a first plunger rod located in the first chamber, the first plunger rod having a first dose tab that extends outside of the first chamber through the first slot, the first dose tab being usable to move the first plunger rod within the first chamber to vary the first predetermined size to set the dose of the non-liquid medicine; and
   a coupling connected with the body and being sized and shaped to removably connect the body with the container, the coupling having a first aperture, at least one of the coupling and the body being rotatable between a first position, in which the first aperture is at least partially aligned with the first chamber, and a second position, in which the first aperture is not aligned with the first chamber.

2. A device according to claim 1, wherein the body further comprises:
   a second chamber of a second predetermined size and configured to contain the non-liquid medicine, a second part of the outer wall of the body being shared with the second chamber, a second slot being defined through the second part of the outer wall of the body shared with the second chamber;
   a second plunger rod located in the second chamber, the second plunger rod having a second dose tab that extends outside of the second chamber through the second slot, the second dose tab being usable to move the second plunger rod within the second chamber to vary the second predetermined size to set the dose of the non-liquid medicine; and
   wherein the coupling further comprises a second aperture, at least one of the coupling and the body being rotatable between a first position, in which at least one of the first aperture and second aperture is at least partially aligned with one of the first chamber and second chamber, and a second position, in which at least one of the first aperture and second aperture is not aligned with one of the first chamber and second chamber.

3. A device according to claim 1, wherein the first plunger rod is located in, and does not extend out of the body.

4. A device according to claim 2, wherein the second plunger rod is located in, and does not extend out of the body.

5. A device according to claim 2, wherein the first predetermined size is larger than the second predetermined size.

6. A device according to claim 1, wherein the first plunger rod has a longitudinal axis, and wherein the first dose tab is parallel to, but not coaxial with the longitudinal axis.

7. A device according to claim 2, wherein the second plunger rod has a longitudinal axis, and wherein the second dose tab is parallel to, but not coaxial with the longitudinal axis.

8. A device according to claim 1, wherein the first plunger rod is moveable within the first chamber over a movement range, and wherein the first dose tab is accessible by a user over the movement range.

9. A device according to claim 2, wherein the second plunger rod is moveable within the second chamber over a movement range, and wherein the second dose tab is accessible by a user over the movement range.

10. A device according to claim 1, wherein the first dose tab is useable by a user to move the first plunger rod in two directions in the first chamber.

11. A device according to claim 2, wherein the second dose tab is useable by a user to move the second plunger rod in two directions in the second chamber.

12. A device according to claim 1, wherein the first plunger rod has a longitudinal axis, and wherein the first dose tab is parallel to, but not coaxial with the longitudinal axis, and wherein the first plunger rod is moveable within the first chamber by force applied to the first dose tab in a direction at least partially transverse to the longitudinal axis.

13. A device according to claim 2, wherein the second plunger rod has a longitudinal axis, and wherein the second dose tab is parallel to, but not coaxial with the longitudinal axis, and wherein the second plunger rod is moveable within the second chamber by force applied to the second dose tab in a direction at least partially transverse to the longitudinal axis.

* * * * *

UNITED STATES PATENT AND TRADEMARK OFFICE
CERTIFICATE OF CORRECTION

PATENT NO. : 10,285,987 B2
APPLICATION NO. : 15/843205
DATED : May 14, 2019
INVENTOR(S) : Gary Payton et al.

Page 1 of 1

It is certified that error appears in the above-identified patent and that said Letters Patent is hereby corrected as shown below:

On the Title Page

Add -- (60) Provisional application No. 62/328,929, filed on Apr. 28, 2016 --

Signed and Sealed this
Twenty-fifth Day of August, 2020

Andrei Iancu
*Director of the United States Patent and Trademark Office*